US006258175B1

(12) United States Patent
Lightner

(10) Patent No.: US 6,258,175 B1
(45) Date of Patent: Jul. 10, 2001

(54) METHOD TO PRODUCE FERMENTABLE SUGARS FROM A LIGNOCELLULOSE MATERIAL

(76) Inventor: Gene E. Lightner, 706 SW. 296th St., Federal Way, WA (US) 98023

( * ) Notice: Subject to any disclaimer, the term of this patent is extended or adjusted under 35 U.S.C. 154(b) by 0 days.

(21) Appl. No.: 09/433,327

(22) Filed: Nov. 3, 1999

(51) Int. Cl.[7] ................................ C07H 3/00; C13K 1/02
(52) U.S. Cl. ................................................ 127/37; 435/165
(58) Field of Search ................................ 127/37; 435/165

(56) References Cited

U.S. PATENT DOCUMENTS 4,608,245 * 8/1986 Gaddy et al. ......................... 423/531
6,007,636 * 12/1999 Lightner ................................. 127/37

* cited by examiner

*Primary Examiner*—David Brunsman

(57) ABSTRACT

A method is presented that will produce fermentable sugars from a lignocellulose material employing concentrated sulfuric acid to dissolve cellulose and hemicellulose in a lignocellulose material followed by hydrolysis in place to depolymerize the cellulose and hemicellulose to produce fermentable sugars and separated water insoluble solids. The concentrated sulfuric acid, containing sugars and water insoluble solids, is then combined with ethanol from a previous extraction, containing ethanol, to precipitate the sugars and is co-mingled with the water insoluble solids to form solids and a solution of ethanol and sulfuric acid. The solution of ethanol and sulfuric acid containing solids is then separated to produce solids and a solution containing ethanol and sulfuric acid. The separated solids are extracted with ethanol and will substantially extract residual sulfuric acid from the separated solids creating ethanol extracted solids and provide an extractate to precipitate additional sugars. The solution of ethanol and sulfuric acid separated from the solids will thereupon be parted to produce ethanol and concentrated sulfuric acid, substantially devoid of ethanol, for intended recycle. Water insoluble solids are produced by the method.

20 Claims, 4 Drawing Sheets

METHOD TO PRODUCE FERMENTABLE SUGARS FROM A LIGNOCELLULOSE MATERIAL

BACKGROUND OF THE INVENTION

Throughout the world there is increasing interest in converting renewable lignocellulose material to usable products such as ethanol. Conversion of wood to ethanol has been practiced during wartime due to a shortage of liquid fuels. Reported in Ind. & Eng. Chem. Vol. 38 No. 9, page 890 (1946). Because of high pressures, high temperatures, low yields and consumption of chemicals the conversion was found to be uneconomical for peacetime use. Present day interest in hydrolysis of Biomass, often termed lignocellulose material, is to provide an alternative fuel source to avoid dependence on unreliable imported petroleum crude oil for liquid fuels. Biomass often contains hemicellulose and lignins accompanying the cellulose contained in the lignocellulose material. Biomass is a term used to describe renewable material containing cellulose. For example, paper, pulp, wood waste, sawdust, municipal solid waste (MSW) and agricultural wastes, all are herein refereed to as lignocellulose material. The hemicellulose and amorphous cellulose of a lignocellulose material is easily hydrolyzed to form sugars for fermentation in a process called pre-hydrolysis which leaves a residue containing lignins and un-hydrolyzed crystalline cellulose. Pre-hydrolysis consists of the reaction of water with a lignocellulose material in the presence of a catalyst, usually sulfuric acid. The residue from pre-hydrolysis contains lignins, un-hydrolyzed hemicellulose and un-hydrolyzed cellulose and is consequently a lignocellulose material.

It is well known that a high concentration of sulfuric acid will hydrolyze cellulose and hemicellulose at low temperatures to produce sugars for fermentation.

A state of the art process being developed by workers at the University of Arkansas is reported in FY 1997 BIOCHEMICAL conversion/ALCOHOL FUELS PROGRAM, Annual Report page 85. It employs high concentration of sulfuric acid to convert corn stover to sugars. Described is a scheme to separate sugars contained in the concentrated sulfuric acid using a heavy boiling solvent to dissolve the sulfuric acid and a low boiling solvent to dissolve the heavy boiling solvent. They also reported that this method has a loss of solvents and a loss of sulfuric acid, which is neutralized with lime. Reported in the above named report, on page A-15, is a plan by TVA to develop a high concentration of sulfuric acid process. The current focus of TVA is to develop an inexpensive process for recovering the high concentration of sulfuric acid. Thus recovery of the sulfuric acid is reported as an unsolved problem. The problem with these methods is the failure to cost effectively recover concentrated sulfuric acid. Consequently it is believed that no satisfactory recovery method has yet been developed.

The present interest is related to concentrated sulfuric acid used to produce fermentable sugars contained in a lignocellulose material and the separation of sulfuric acid from sugars formed. Solids, substantially free from sulfuric acid, contain precipitated fermentable sugars. The fermentable sugars are then dissolved by a broth from fermentation. The dissolved fermentable sugars are then fermented in a fermentation vessel to form a fermentation broth. The concentrated sulfuric acid, separated from the fermentable sugars, is recycled to produce additional fermentable sugars.

Thus many of the limitations and disadvantages of the prior art to recover sulfuric acid employed to produce fermentable sugars will be obviated.

Therefore an object of this invention is to employ concentrated sulfuric acid to produce fermentable sugars from a lignocellulose material.

Another object of this invention is to economically separate sulfuric acid from lignins and sugars formed from a lignocellulose material and to supply concentrated sulfuric acid for recycle.

An additional object of this invention is to ferment sugars formed from a lignocellulose material contained in sterilized ethanol extracted solids.

A further object of this invention is to produce lignins substantially free of sugars and sulfuric acid formed from a lignocellulose material.

Still another object of this invention is to produce a yield of hydrolysis of cellulose and hemicellulose nearing 100%.

Yet another object of this invention is to operate the method in a closed environment.

Additionally another object of this invention is to operate and accomplish low energy consumption.

With the above and other objects in view, this invention relates to the novel features and alternatives and combinations presently described in the brief description of the invention.

BRIEF DESCRIPTION OF THE INVENTION

The present invention, in its broadest aspect, will establish a method to convert lignocellulose materials, implying concentrated sulfuric acid, into fermentable sugars from cellulose and hemicellulose contained in lignocellulose materials and to separate water insoluble solids also contained in the lignocellulose materials. Key features are:

Substantially freeing fermentable sugars from the concentrated sulfuric acid and recycling to reuse recovered concentrated sulfuric acid.

Hemicellulose accompanying cellulose in a lignocellulose material and will be converted to fermentable sugars.

Recycling to reuse ethanol essential to the method and withdrawal of water insoluble solids substantially free of sugars and chemicals integral to the method.

In this invention, concentrated sulfuric acid is recycled for employment in dissolving cellulose and hemicellulose contained in lignocellulose materials followed by hydrolyzing dissolved cellulose and hemicellulose in place to form fermentable sugars in concentrated sulfuric acid. An extractate containing ethanol and sulfuric acid is combined with concentrated sulfuric acid containing sugars to solidify sugars and inert water insoluble solids to form a solution of ethanol and sulfuric acid containing solidified sugars and water insoluble solids. After parting the solids from the solution, the solids are extracted by ethanol to produce sulfuric acid free solids and an extractate for foregoing employment. The ethanol extracted fermentable sugars from the extracted solids are dissolved in a fermentation broth to produce a broth containing water insoluble solids. Upon separation, the dissolved fermentable sugars containing ethanol and water insoluble solids are separated into water insoluble solids and the broth of dissolved fermentable sugars containing ethanol. The dissolved fermentable sugars, contained in the broth, are then fermented to produce additional fermentation broth. Additionally, separated water insoluble solids are extracted with an aqueous solution to form an aqueous extractate for separate fermentation followed by distillation stripping of the separate fermentation broth for substantial removal of ethanol in the overhead and to produce a bottoms of an aqueous solution for the previous extraction The extracted water insoluble solids, including lignins, are substantially free of ethanol, sugars and sulfuric acid. pH of the fermentation broth will be controlled at an established predetermined level and maintained by feedback from the fermentation broth by addition of calcium carbonate or ammonia or sulfuric acid. Nutrient composition and activity of microorganisms required for fermentation in the fermentation broth is controlled at an established predetermined level.

DESCRIPTION OF THE PREFERRED EMBODIMENT

The preferred embodiment of this invention embodies mixing together concentrated sulfuric acid with a lignocellulose material containing cellulose followed by hydrolysis in place to form fermentable sugars. This will depolymerize the cellulose and hemicellulose accompanying the cellulose to provide fermentable sugars and water insoluble solids. The invention embodies adding an extractate from a previous counter flow ethanol extraction containing ethanol which is soluble in concentrated sulfuric acid but substantially insoluble in the fermentable sugars to form solids containing a precipitate of the fermentable sugars and water insoluble solids in a solution of sulfuric acid and ethanol. The invention embodies setting apart to substantially divide the solids from the solution containing sulfuric acid and ethanol and then to extract residual sulfuric acid from the solids with supplementary ethanol to form extracted solids and a resulting extractate to precipitate additional fermentable sugars.

One embodiment of the invention incorporates dissolving the heretofore extracted solids containing precipitated fermentable sugars by adding to a fermentation broth which includes water and ethanol, employed as a solvent, to produce a mixture of dissolved fermentable sugars, ethanol, water and water insoluble solids. The invention provides a procedure for dividing the mixture to substantially divide water insoluble solids and to produce a mixture of dissolved fermentable sugars, ethanol, and water. Divided water insoluble solids are removed and counter flow extracted with an aqueous solution composed chiefly of water. The aqueous solution extracted water insoluble solids are substantially devoid of dissolved fermentable sugars and ethanol. The aqueous extractate contains dissolved fermentable sugars and ethanol and is advanced to a fermentation vessel for fermentation followed by removal of fermentation broth from the fermentation vessel for distillation to strip and to produce ethanol in the overhead and to produce a bottoms of an aqueous solution. The mixture of dissolved fermentable sugars is fermented separately to produce a fermentation broth, with means for partial removal of ethanol from the fermentation broth, to be employed for dissolving additional extracted precipitated fermentable sugars.

An alternative embodiment of the invention incorporates adding the solids, containing extracted precipitated fermentable sugars, to a vessel, containing a fermentation broth to consequently dissolve the fermentable sugars for fermentation in the fermentation broth and removing the water insoluble solids from the vessel. The water insoluble solids, adhering to fermentation broth, are removed from the vessel and then added to a separate vessel for fermentation. Fermentation broth and water insoluble solids are removed from the separate vessel and subjected to distillation to strip and produce ethanol in the overhead which is condensed to form liquid ethanol and to produce a bottoms of water insoluble solids and an aqueous solution for subsequent extraction or discarding.

Means for separating ethanol from the solution containing sulfuric acid and ethanol includes vaporization and condensation of the ethanol vapor for recycle and moreover produces concentrated sulfuric acid for recycle. One means to separate ethanol from the solution involves extracting the solution with an oil, which is insoluble in the concentrated sulfuric acid but soluble in ethanol. Extraction of the solution by counter flow of oil produces an extractate containing oil and ethanol and a raffinate having two phases: the upper phase contains oil, the lower phase contains concentrated sulfuric acid, substantially devoid of the ethanol to provide concentrated sulfuric acid for recycle. Oil extractate is then heated to evaporate ethanol vapor, which is then condensed to form ethanol for recycle. The oil, substantially devoid of the ethanol, flows from the evaporator bottoms and, after cooling, is used for additional extraction.

An alternate means to separate ethanol from the solution incorporates vaporization and condensation of the ethanol vapor for reuse. This alternate means to separate ethanol from the solution incorporates vaporization from an evaporator of the ethanol to produce the concentrated sulfuric acid substantially devoid of ethanol. The liquid is evaporated to form ethanol vapor and then followed by condensation of the ethanol vapor for reuse. The evaporator bottoms contains the concentrated sulfuric acid substantially devoid of the ethanol to provide concentrated sulfuric acid for recycle. The overhead form ethanol vapor is followed by condensation of the ethanol vapor for reuse.

BRIEF DESCRIPTION OF THE DRAWINGS

The features that are considered characteristic of this invention are set forth in the appended claims. This invention, however, both as to its origination and method of operations as well as additional advantages will best be understood from the following description when read in conjunction with the accompanying drawings in which:

DETAILED DESCRIPTION OF THE PREFERRED EMBODIMENT

In the preferred embodiment of the present invention, a supply of lignocellulose material substantially free of water contains cellulose and frequently contains hemicellulose and lignins. The temperature range for conversion of a lignocellulose material is about 20° C. to about 80° C. In the diagram, rectangles represent stages or functions of the present invention and not necessarily separate components. Arrows indicate direction of flow of material in the method.

Figure 1:
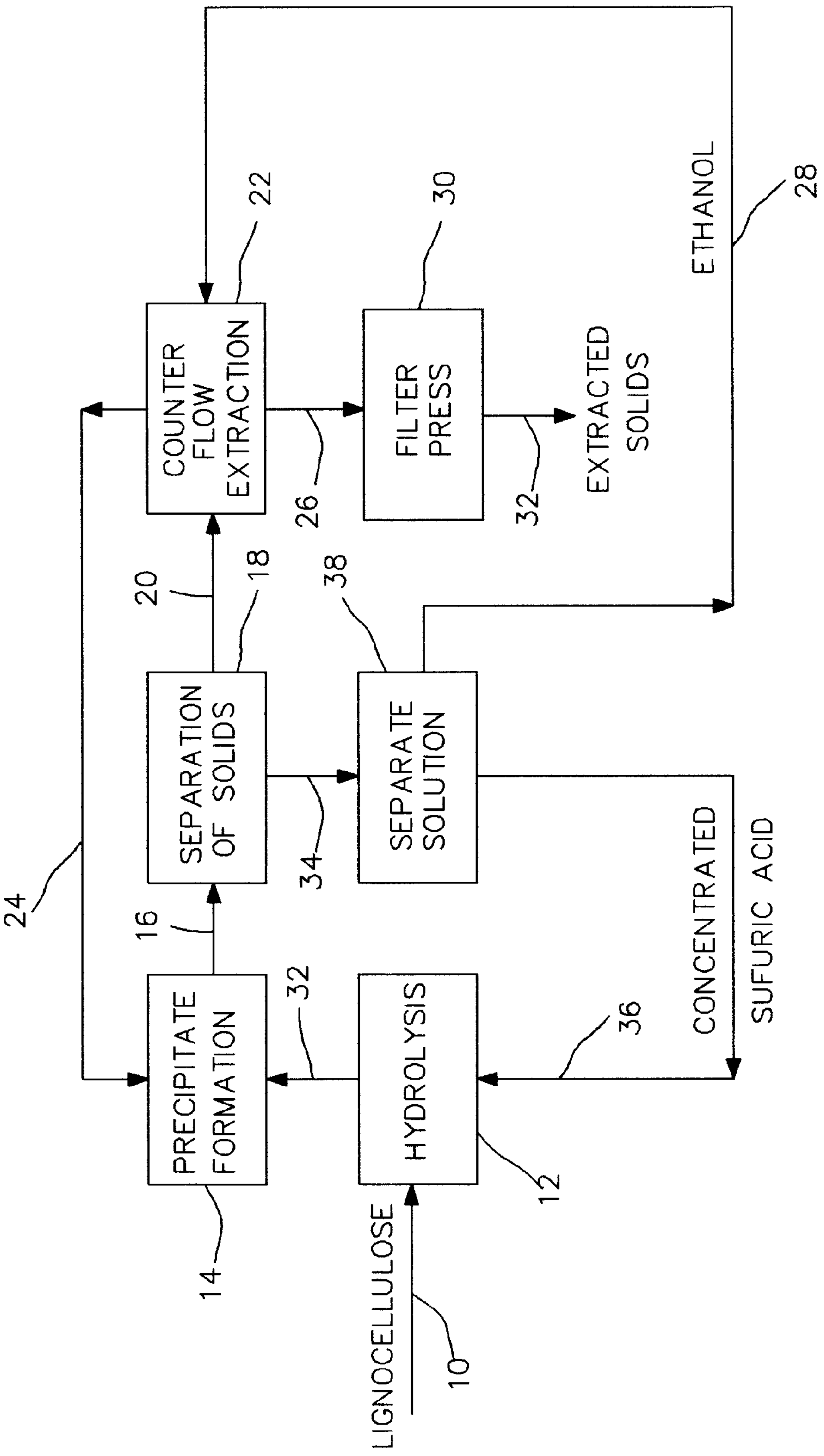
FIG. 1 is a flow sheet denoting the invention as set forth in the appended claims.

The flow diagram of FIG. 1 illustrates the general preferred embodiment of the present invention.

Referring to FIG. 1, lignocellulose material 10, is conveyed into a hydrolysis stage 12, where concentrated sulfuric acid 36, is forwarded to the hydrolysis stage 12 which depolymerizes cellulose and hemicellulose contained in the lignocellulose material 10 to form a mixture 32 containing fermentable sugars and solids insoluble in water then flows to a stage for precipitate formation 14

Precipitation of the fermentable sugars is formed by addition of an extractate 24 containing ethanol and sulfuric acid from an ethanol counter flow extraction stage 22. A solution containing ethanol and sulfuric acid and a precipitation and solids insoluble in water 16 flows to a separation of solids stage 18 and then separates a solution containing ethanol and sulfuric acid 34, for subsequent separation of the solution by stage 38, which separates ethanol 28 which then flows to the ethanol counter flow extraction stage 22 where ethanol insoluble solids containing ethanol and sulfuric acid 20 are extracted by ethanol 28, typically extracted by counter flow of ethanol. Ethanol insoluble solids containing ethanol 26 are transferred to a filter press stage 30 to yield extracted solids 32. Concentrated sulfuric acid 36 from the separation of the solution by stage 38 is conveyed to the hydrolysis stage 12. Separation of the solution 34 to ethanol and concentrated sulfuric acid can be achieved by several means. The means includes evaporation of the solution to provide ethanol and sulfuric acid and extraction of the solution employing an oil, insoluble in sulfuric acid but soluble in ethanol to provide recycle of concentrated sulfuric acid substantially devoid of ethanol. The extracted oil contains ethanol for subsequent evaporation to form ethanol for recycle. Other means include diffusion membranes having ion exchange characteristics, membranes akin to reverse osmosis, electro dialysis and any combination of the membranes or evaporation means. The solution containing ethanol and sulfuric acid and a precipitation and solids insoluble in water 16 flowing to a separation of solids stage 18 for separation of the solids 20 from the solution containing ethanol and sulfuric acid 34. Separation of the solids can be produced by settling or by filtration.

Figure 2:
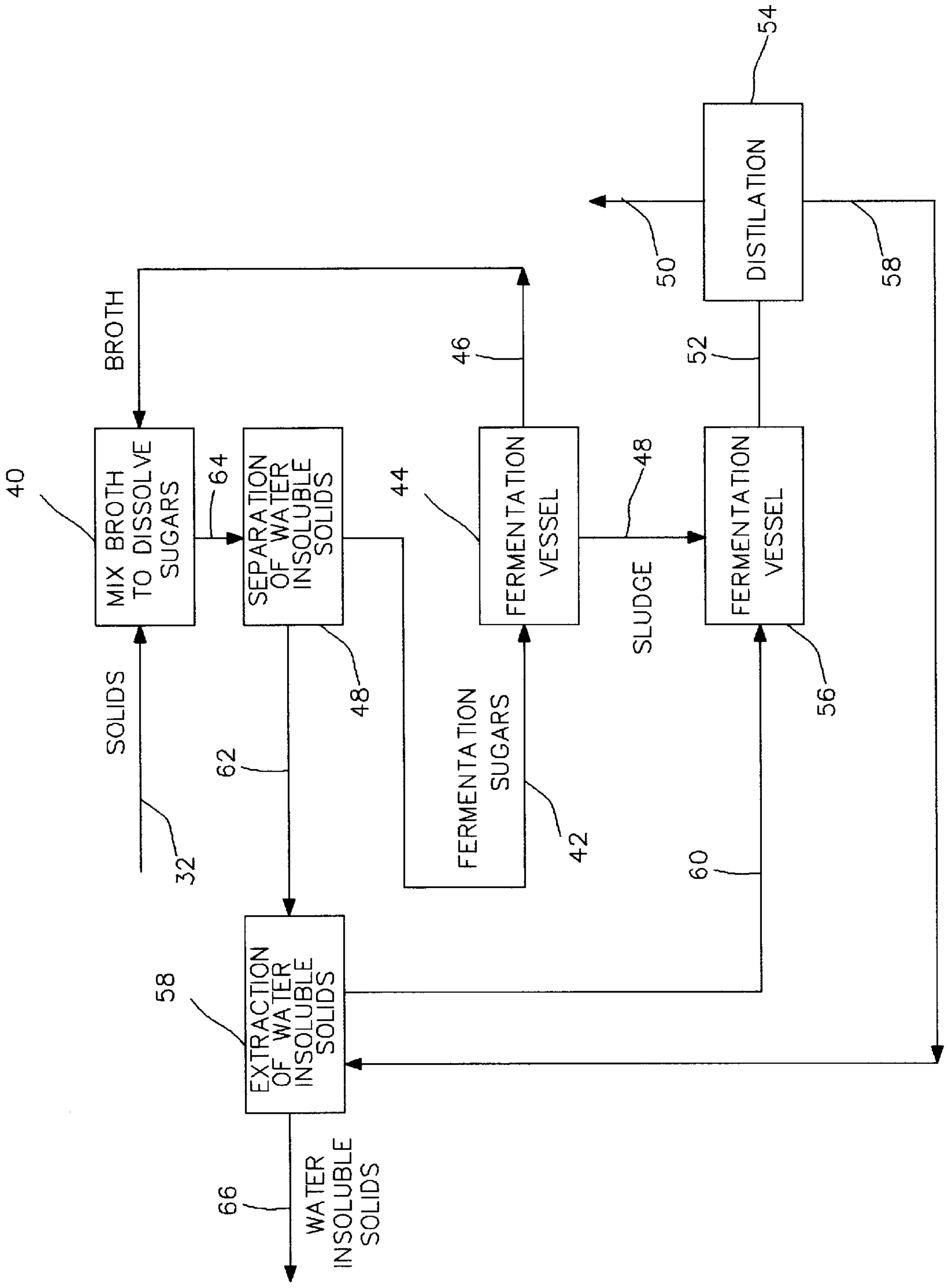
FIG. 2 is a flow sheet denoting a method for fermentation of sugars.

Referring to FIG. 2, a flow sheet denoting a method for fermentation of sugars is shown. Solids 32 from FIG. 1 are directed to a broth mixer 40 to dissolve sugars contained in the solids. The resulting mixture 64 is then transferred to 48 to achieve separation of water insoluble solids where the water insoluble solids 62 are conveyed to extraction of water insoluble solids 58 to produce extracted water insoluble solids 66 and an extractate 60 transported to a fermentation vessel 56. Where fermentation broth and sludge 52 is conveyed to distillation 54 where overhead vapor is condensed to yield a condensate containing ethanol 50 and a bottoms 58 conveyed to extraction of water insoluble solids 58. Fermentation sugars, dissolved in fermentation broth, 42 are supplied to a fermentation vessel 44 to produce a fermentation both 46 with partial removal of ethanol from the fermentation both to maintain a constant ethanol concentration and then transferred to the mixer 40 to dissolve additional fermentable sugars contained in solids 32. pH of the fermentation broth way be controlled and maintained by feedback from the fermentation broth by addition of calcium carbonate or ammonia or sulfuric acid to the solids.

Figure 3:
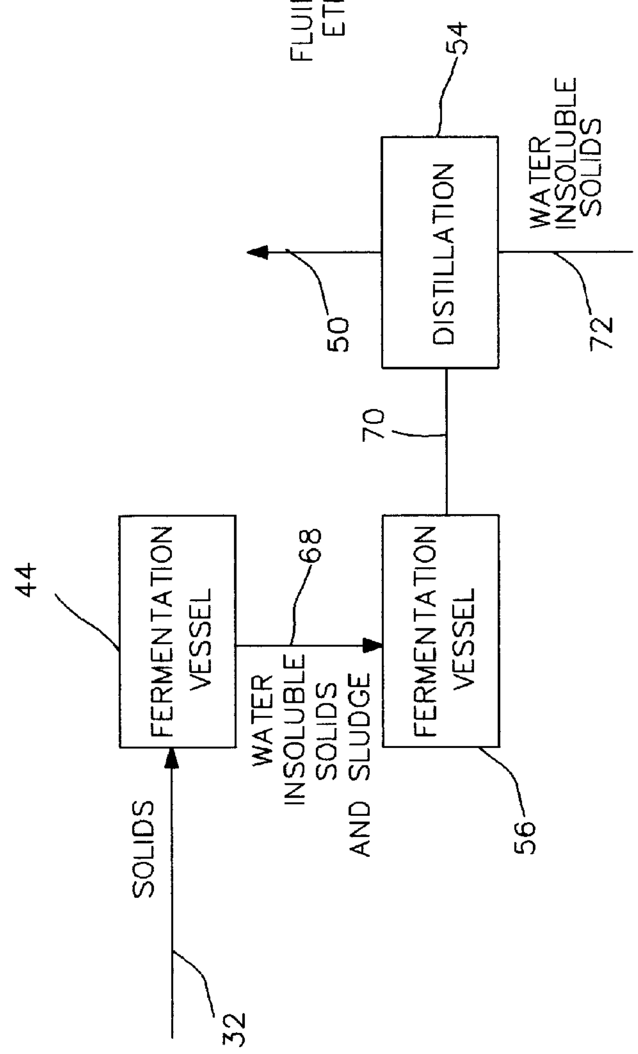
FIG. 3 is a flow sheet denoting an alternative method for fermentation of sugars.

Referring to FIG. 3, a flow sheet denoting a method for fermentation of sugars is shown. Solids 32 from FIG. 1 is directed to a fermentation vessel 44 containing fermentation both with partial removal of ethanol from the fermentation both, to maintain at a constant ethanol concentration, and to produce water insoluble solids and sludge 68 which is transferred to a second fermentation vessel 56 where insoluble solids and sludge 70 is forwarded to distillation 54 where overhead vapor is condensed to yield a condensate containing ethanol 50 and a bottoms 72 for removal of water insoluble solids and for discarding of the aqueous bottoms. The vessel is maintained at a constant volume by withdrawal of water insoluble solids. The vessel may be operated continuously and the contained fermentation broth is maintained at a substantially constant ethanol concentration by withdrawal of ethanol.

Figure 4:
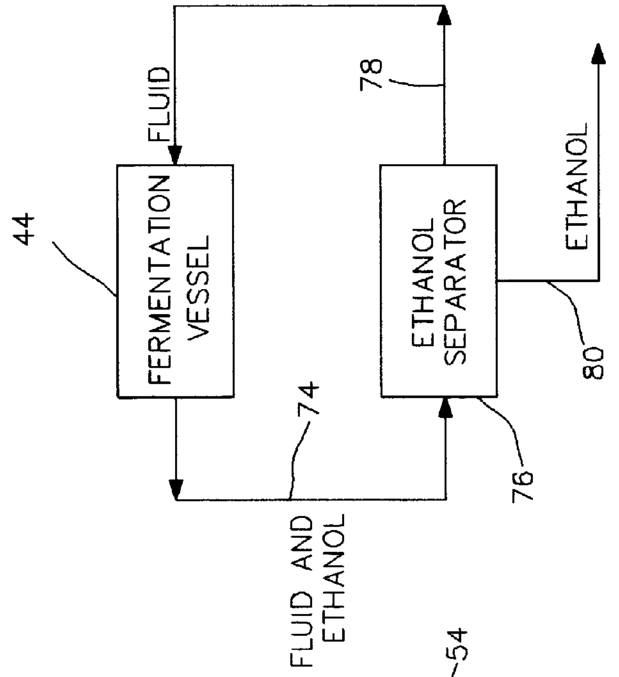
FIG. 4 is a flow sheet denoting a method for separation of ethanol.

Referring to FIG. 4, a flow sheet denoting a method for separation of ethanol from fermentation broth is shown. A fermentation vessel 44 from FIG. 1 containing fermentation both with partial separation of ethanol is mingled with a fluid insoluble in the fermentation broth 78. The fluid containing ethanol 74 is transported to a separation stage 76 to separate and free ethanol 80. The fluid can be gaseous such as carbon dioxide or an oil insoluble in a fermentation broth.

Figure 5:
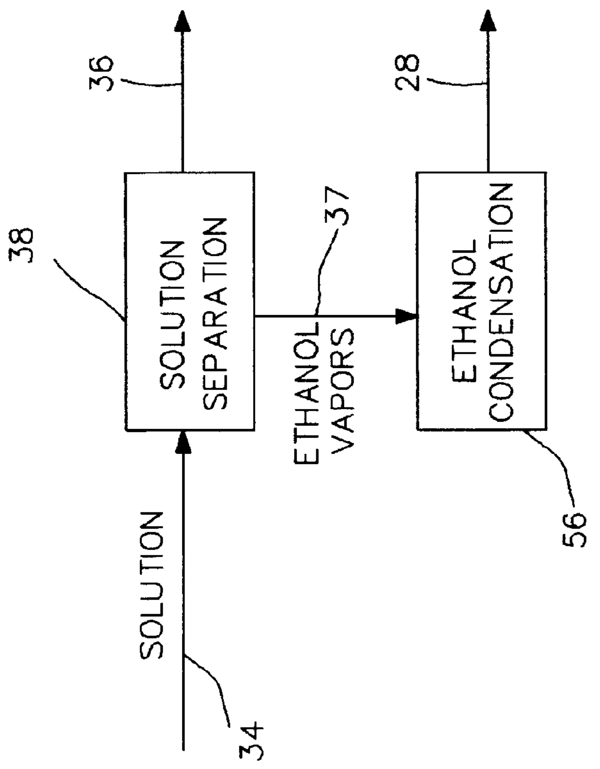
FIG. 5 is a flow sheet denoting a method for separation of a solution.

Referring to FIG. 5, a flow sheet denoting a method for separation of a solution 34 from FIG. 1 containing ethanol and sulfuric acid is shown. The solution is fed to solution separation stage 38 where by evaporation and condensation of the ethanol vapor 37 forms liquid ethanol 28. After evaporation and separation of the ethanol concentrated sulfuric acid substantially free of ethanol 36 is formed. Solution separation is achieved by vaporization.

Figure 6:
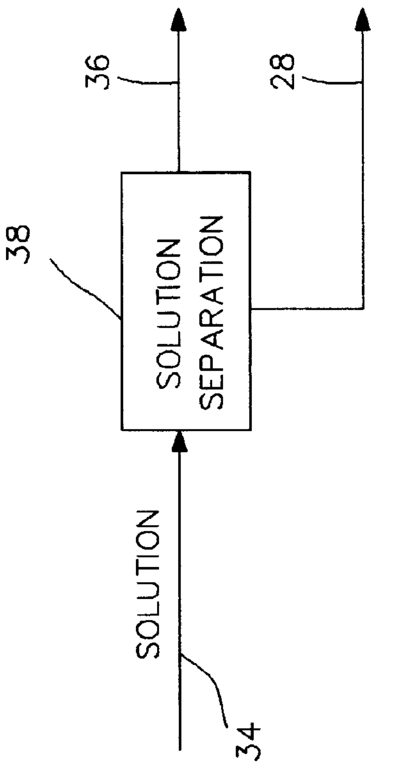
FIG. 6 is a flow sheet denoting an alternative method for separation of a solution.

Referring to FIG. 6, a flow sheet denoting a method for separation of a solution 34 from FIG. 1 containing ethanol and sulfuric acid is shown. The solution is fed to a solution separation stage 38 where by diffusion of sulfuric acid, separation of ethanol is achieved, to form concentrated sulfuric acid substantially free of ethanol 36 and ethanol substantially free of sulfuric acid 28. Solution separation is achieved by diffusion.

The following examples are set forth to illustrate more clearly the principles and practice of the invention. Where parts or quantities are mentioned, the parts or quantities are by weight.

EXAMPLE 1

Ten grams of oven dried maple saw dust is added to about 100 grams of 72% sulfuric acid in a 250 cc beaker at room temperature, with stirring, to hydrolyze and dissolve the sugars. After about twelve hours, the contents of the beaker is combined with about 100 grams of a synthetic extractate composed of about 90% denatured ethanol and about 10% of 72% sulfuric acid to form a precipitate of sugars and water insoluble solids to form solids. The contents of the beaker are then filtered to separate the solids from the filtrate. The filtrate is then discarded. The solids contains about 90% denatured ethanol and about 10% of 72% sulfuric acid. The solids are then extracted by 100 grams of denatured ethanol to extract adhering acid from the solids. The extractate is then discarded. The extracted solids, containing denatured ethanol, is then mixed with about 100 grams of a synthetic broth composed of about 10% denatured ethanol in water to form a mixture of ethanol and dissolved sugars and water insoluble solids. The mixture is filtered to part water insoluble solids and forms a synthetic broth for fermentation containing ethanol and water and dissolved sugars and would normally be fermented. The filtrate is then discarded. The water insoluble solids are then extracted with water to form water insoluble solids containing water and an extractate composed of about 90% water and about 5% of denatured ethanol and about 5% of dissolved sugars. The extractate would normally be fermented but is herein discarded.

EXAMPLE 2

Maple sawdust is subjected to pre-hydrolysis in a solution of about 0.5% sulfuric acid, at about 100° C. for about three hours, to form a lignocellulose material which is then separated from the solution and then oven dried. The solution is then discarded. Ten grams of the oven dried lignocellulose material is added to about 100 grams of 72% sulfuric acid in a 250 cc beaker at room temperature, with stirring, to hydrolyze and dissolve the sugars. After about twelve hours, the contents of the beaker is combined with about 100 grams of a synthetic extractate composed of about 90% denatured ethanol and about 10% of 72% sulfuric acid to form a precipitate of sugars and water insoluble solids to form solids. The contents of the beaker are then filtered to separate the solids from the filtrate. The filtrate is then discarded. The solids contains about 90% denatured ethanol and about 10% of 72% sulfuric acid. The solids are then extracted by 100 grams of denatured ethanol to extract adhering acid from the solids The extractate is then discarded. The extracted solids, containing denatured ethanol, is then mixed with about 100 grams of a synthetic broth composed of about 10% denatured ethanol in water to form a mixture of ethanol and dissolved sugars and water insoluble solids. The mixture is filtered to part water insoluble solids and forms a synthetic broth for fermentation containing ethanol and water and dissolved sugars and would normally be fermented. The filtrate is then discarded. The water insoluble solids are then extracted with water to form water insoluble solids containing water and an extractate composed of about 90% water and about 5% of denatured ethanol and about 5% of dissolved sugars. The extractate would normally be fermented but is herein discarded.

What is claimed is:

1. A method to produce fermentable sugars from a lignocellulose material employing concentrated sulfuric acid, which comprises:

Providing a lignocellulose material, and

Providing concentrated sulfuric acid

Combining said concentrated sulfuric acid with said lignocellulose material to dissolve cellulose and hemicellulose contained in a lignocellulose material followed by hydrolysis in place to depolymerize the cellulose and hemicellulose to produce fermentable sugars, and mixing together said concentrated sulfuric acid containing said fermentable sugars with an extractate from a previous extraction containing ethanol which is soluble in the sulfuric acid but substantially insoluble in the fermentable sugars and water insoluble solids from the lignocellulose to form solids containing said fermentable sugars and said water insoluble solids, and Separating to substantially divide said solids from the solution containing sulfuric acid and ethanol, and extracting, by counter flow, the heretofore separated solids with supplementary ethanol to substantially extract residual sulfuric acid from the heretofore separated solids and forming an extractate for subsequent employment to form solids of fermentable sugars, and parting the solution of ethanol and concentrated sulfuric acid from which the heretofore separated solids have been removed, and creating ethanol extracted solids whereby solids containing fermentable sugars and water insoluble solids substantially free of sulfuric acid are produced from a lignocellulose material.

2. The method of claim 1 where said separating means to part said solution from ethanol and concentrated sulfuric acid solution is parted to substantially free ethanol from sulfuric acid to provide sulfuric acid for recycle and ethanol.

3. The method of claim 1 where said ethanol extracted solids containing fermentable sugars is hydrolyzed to produce fermentable sugars for fermentation.

4. The method of claim 1 where said ethanol extracted solids containing fermentable sugars is sterilized.

5. The method of claim 1 wherein said ethanol extracted solids is added to a fermentation broth located in a fermentation vessel containing a fermentation broth.

6. The method of claim 5 wherein said fermentation broth is established and maintained at a predetermined pH.

7. The method of claim 5 wherein said fermentation broth nutrient composition is established and maintained at a predetermined concentration in said fermentation broth.

8. The method of claim 5 wherein yeast, enzymes or microorganisms activity required for fermentation is established maintained at a predetermined activity in said fermentation broth.

9. The method of claim 5 wherein contents of said fermentation vessel is maintained at a constant volume by withdrawal of the water insoluble solids and broth from the fermentation vessel wherein the water insoluble solids and fermentation broth withdrawn is added to a separate fermentation vessel.

10. The method of claim 5 wherein said fermentation vessel is operated continuously.

11. The method of claim 5 wherein water insoluble solids, contained in said extracted solids, are located at the bottom of said fermentation vessel.

12. The method of claim 5 wherein said fermentation broth is, by withdrawal of ethanol, established and maintained at a predetermined ethanol concentration.

13. The method of claim 5 where said fermentation broth is subjected to partial separation of ethanol by mingling the fermentation both with a fluid insoluble in the fermentation broth to partially separate ethanol from the fermentation broth.

14. The method of claim 13 where said fluid insoluble in the fermentation broth is a gaseous fluid.

15. The method of claim 13 where said fluid insoluble in the fermentation broth is an oil.

16. The method of claim 1 where said ethanol extracted solids is mixed with a fermentation broth to dissolve said sugars to form a solution of fermentable sugars and to contain water insoluble solids where said water insoluble solids are substantially separated from said solution of fermentable sugars and the heretofore fermentable sugar solution, separated from the water insoluble solids, is added to a fermentation vessel.

17. The method of claim 16 wherein said fermentation vessel is operated continuously.

18. The method of claim 16 wherein said fermentation broth is established and maintained at a predetermined ethanol concentration.

19. The method of claim 1 where said solution containing sulfuric acid and ethanol is substantially separated by evaporation to provide recycle of ethanol and concentrated sulfuric acid.

20. The method of claim 1 where said solution containing sulfuric acid and ethanol is substantially separated by membrane to provide ethanol and concentrated sulfuric acid.

* * * * *